(12) United States Patent
Brennan et al.

(10) Patent No.: US 6,695,793 B2
(45) Date of Patent: Feb. 24, 2004

(54) GUIDE CATHETER FOR PLACING CARDIAC LEAD

(75) Inventors: Lawrence Brennan, Temecula, CA (US); Fozan El-Nounou, Sunnyvale, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 222 days.

(21) Appl. No.: 09/918,988

(22) Filed: Jul. 31, 2001

(65) Prior Publication Data

US 2003/0028153 A1 Feb. 6, 2003

(51) Int. Cl.$^7$ .............................. A61M 25/088
(52) U.S. Cl. ................ 600/585; 128/899; 606/129; 604/532
(58) Field of Search .................. 607/119, 122, 607/126, 127, 128; 600/585; 128/899; 606/129; 604/264, 523, 532, 175, 104, 105

(56) References Cited

U.S. PATENT DOCUMENTS

| | | | |
|---|---|---|---|
| 2,541,691 A | * 2/1951 | Eicher .......................... 27/24.2 |
| 3,974,834 A | 8/1976 | Kane |
| 4,781,682 A | * 11/1988 | Patel ..................... 604/103.05 |
| 4,973,301 A | * 11/1990 | Nissenkorn ..................... 604/8 |
| 5,122,125 A | * 6/1992 | Deuss .......................... 604/524 |
| 5,215,103 A | * 6/1993 | Desai ........................... 606/46 |
| 5,431,683 A | 7/1995 | Bowald et al. |
| 5,458,574 A | * 10/1995 | Machold et al. ........ 604/101.03 |
| 5,509,900 A | * 4/1996 | Kirkman ...................... 604/104 |
| 5,545,206 A | 8/1996 | Carson |
| 5,755,766 A | 5/1998 | Chastain et al. |
| 5,759,202 A | 6/1998 | Schroeppel |
| 5,775,327 A | * 7/1998 | Randolph et al. ............ 600/374 |
| 5,800,495 A | 9/1998 | Machek et al. |
| 5,800,497 A | 9/1998 | Bakels et al. |
| 5,803,928 A | 9/1998 | Tockman et al. |
| 5,931,864 A | 8/1999 | Chastain et al. |
| 5,935,160 A | 8/1999 | Auricchio et al. |
| 6,001,085 A | 12/1999 | Lurie et al. |
| 6,070,104 A | 5/2000 | Hine et al. |
| 6,122,552 A | 9/2000 | Tockman et al. |
| 6,240,321 B1 | 5/2001 | Janke et al. |
| 6,343,226 B1 | * 1/2002 | Sunde et al. ................. 600/378 |
| 2002/0077691 A1 | * 6/2002 | Nachtigall .................. 623/1.12 |

FOREIGN PATENT DOCUMENTS

| EP | 0 653 223 A2 | 7/1994 |
|---|---|---|
| WO | WO 99/55412 | 11/1999 |

* cited by examiner

*Primary Examiner*—Kennedy Schaetzle
(74) *Attorney, Agent, or Firm*—Thomas J. Nikolai; Nikolai & Mersereau, P.A.

(57) ABSTRACT

An improved guide catheter provides a distal tip with one or more members that assist a surgeon with locating and inserting the guide catheter through the ostium in the wall of the right atrium that leads to the coronary sinus of the heart. The guide catheter is used to implant a cardiac lead so that its electrodes are positioned in the vasculature associated with the left side of the heart.

9 Claims, 6 Drawing Sheets

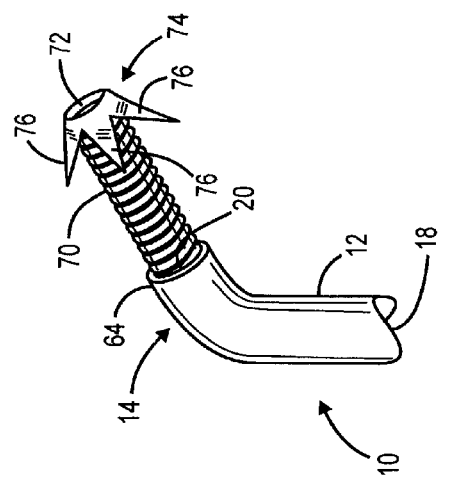
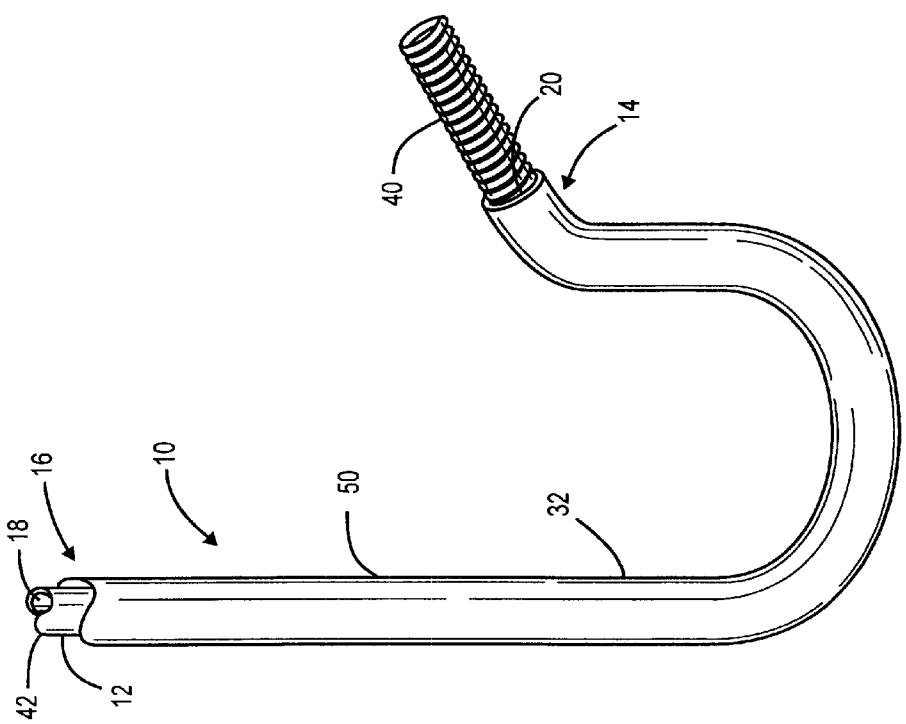

GUIDE CATHETER FOR PLACING CARDIAC LEAD

BACKGROUND OF THE INVENTION

I. Field of the Invention

The present invention relates to the treatment of congestive heart failure. More specifically, it relates to the guide catheter used to properly position a cardiac lead in the heart so that when the lead is electrically coupled to a cardiac rhythm management device, electrical pulses are delivered from the cardiac rhythm management device to the proper location of the heart.

II. Discussion of the Prior Art

Congestive heart failure (CHF) is a progressive weakening of the heart and loss of its ability to efficiently pump blood to the rest of the body. As CHF progresses, the heart becomes enlarged. Eventually, the sequence and timing of electrical pulses that makes a normal heart pump blood efficiently are lost. The ventricles of the heart beat in an irregular and uncoordinated manner so that inadequate blood flow results. CHF causes shortness of breath, fatigue, weakness, and swelling of the legs and abdomen.

CHF is a prevalent disease which is an increasingly important cause of cardiovascular morbidity and mortality. In 1994 there were over 840,000 hospital admissions for CHF. The prognosis of CHF was so poor that the one year survival of severely ill patients was only about 50%.

CHF has a variety of causes and is exacerbated by a variety of conditions. Increased cardiac output caused by anemia, hyperthyroidism, infection or pregnancy can contribute significantly to CHF decompensation. Cardiac events such as arrhythmia, myocardial ischemia or a pulmonary embolism can also lead to heart failure or the exacerbation thereof. Some drugs can also trigger CHF. These include anti-inflammatory drugs, steroids and antibiotics as well as anti-arrhythmic drugs, calcium channel blockers and tricyclic antidepressants. Diet, alcohol consumption, and the patient's failure to observe prescribed fluid restrictions and medication regimens can also trigger CHF.

A variety of treatments have been used to treat CHF. CHF has typically been treated with drugs and changes to the patient's lifestyle. Drugs used in the treatment of CHF include digoxin, diuretics, angiotensin-converting enzyme (ACE) inhibitors, angiotensin receptor blockers, hydralazine and isosorbide dinitrate, beta blockers, and inotropic agents. Lifestyle changes typically relate to restriction of salt in the diet, limiting or eliminating alcohol consumption, and regular exercise.

In acute cases of CHF, surgical strategies have been used. Transplantation of the heart, implementation of ventricular assist devices, cardiomyoplasty, and ventricular remodeling are examples of surgical treatments used to treat CHF.

In many cases, the drug, lifestyle and surgical options listed above have proven to be less than satisfactory. Recently, a new form of treatment has been investigated by the assignee of this invention. This treatment is referred to as bi-ventricular pacing. It involves the use of a heart pacemaker and three leads. One lead is used to deliver electrical signals to the right ventricle. Another lead delivers electrical pulses to the left ventricle. The third is placed in the right atrium. Delivery of pulses to the respective ventricles is sequenced and timed to restore the normal electrical sequence to the heart, thus making the heart pump blood normally and in a more coordinated manner.

Placement of the leads on the exterior of the heart involves highly traumatic surgical procedures. Thus, techniques have been developed for inserting the leads into the appropriate position through the vasculature of the heart. Placing pacing leads into the right side of the heart in this manner, given the current state of the art, is a relatively easy task. However, passing leads through the vasculature of the heart and into proximity with the left ventricle can be quite difficult. Typically, the lead to be coupled to the left ventricle must be advanced through the coronary sinus and great vein of the heart into a descending vein that runs down along the left ventricle to the apex of the heart. The lead must enter the coronary sinus through the ostium located in the right atrium. Locating the ostium in the right atrium can be a difficult and time-consuming task. Reports suggest that even highly skilled surgeons have taken up to three hours locating the ostium using conventional guidewires and guiding catheters.

Heretofore, surgeons have typically used the tip of a guidewire to probe the atrium wall to find the ostium. Once the ostium is found, surgeons have had difficulty advancing the guide catheter into the ostium. Thus, there is a real need for an improved apparatus which can be used to assist the surgeon in locating the ostium and inserting the guide catheter and guidewire through the ostium and into the coronary sinus and great vein of the heart.

SUMMARY OF THE INVENTION

The present invention provides an improved tip for a guide catheter. This improved tip assists the surgeon in locating the ostium of the coronary sinus and advancing the guide catheter through the ostium.

The guide catheter of the present invention, like most guide catheters, includes a flexible wall that surrounds a lumen. The distal tip end of the wall has an opening. The lumen and the opening cooperate so that a guidewire, a cardiac lead or both can be inserted through the lumen and past the distal end of the guide catheter.

In one embodiment, the improved guide catheter of the present invention provides a plurality of fingers that extend distally from the distal end of the wall and surround the opening. The fingers are preferably made of a soft, pliable material. When the fingers contact the wall of the atrium they spread out away from the opening increasing the effective area of the tip of the guide catheter. This larger area, enhances tactile feel, making it easier and less time-consuming to locate the ostium. The fingers are all sufficiently soft and flexible that they fold back against the outside of the guide catheter wall as the tip of the guide catheter is seated in the coronary sinus.

In a second embodiment, the distal end is provided with a plurality of flexible tines that project outwardly from the tubular body of the guide catheter at the distal end of the guide catheter to increase the area of the guide catheter over that of the tubular body. The increased surface area decreased the time required to locate the ostium. Also, the tines can be used to anchor the distal tip of the guide catheter to the edge of the ostium so that the physician can advance a guidewire through the ostium and into the coronary sinus. The physician can then advance the guide catheter over the guidewire and into the coronary sinus.

In a third embodiment, a spring is attached to the distal end of the catheter body. When the spring comes into contact with the atrial wall, it deflects outwardly expanding the surface area of the catheter tip. Again, the expanded area of the catheter tip serves to reduce the time necessary to locate the ostium. When the ostium is located, the spring anchors the guide catheter to the ostium so that the guidewire can easily be advanced into the coronary sinus. The guide catheter can then be advanced into the coronary sinus by sliding it over the guidewire. In a fourth embodiment, both the tines and spring described above are provided.

A better understanding of the present invention will be gained from a review of the following detailed written description of the invention with reference to the accompanying drawings. This description is not intended to be limiting, but is provided to comply with the disclosure requirements of the patent statutes.

BRIEF DESCRIPTION OF THE DRAWINGS

FIG. 7 is a perspective view of a third preferred embodiment of a guide catheter made in conformance with the present invention.

FIG. 8 is a perspective view of a fourth preferred embodiment of a guide catheter made in conformance with the present invention.

DETAILED DESCRIPTION OF THE PREFERRED EMBODIMENTS

Figure 1:
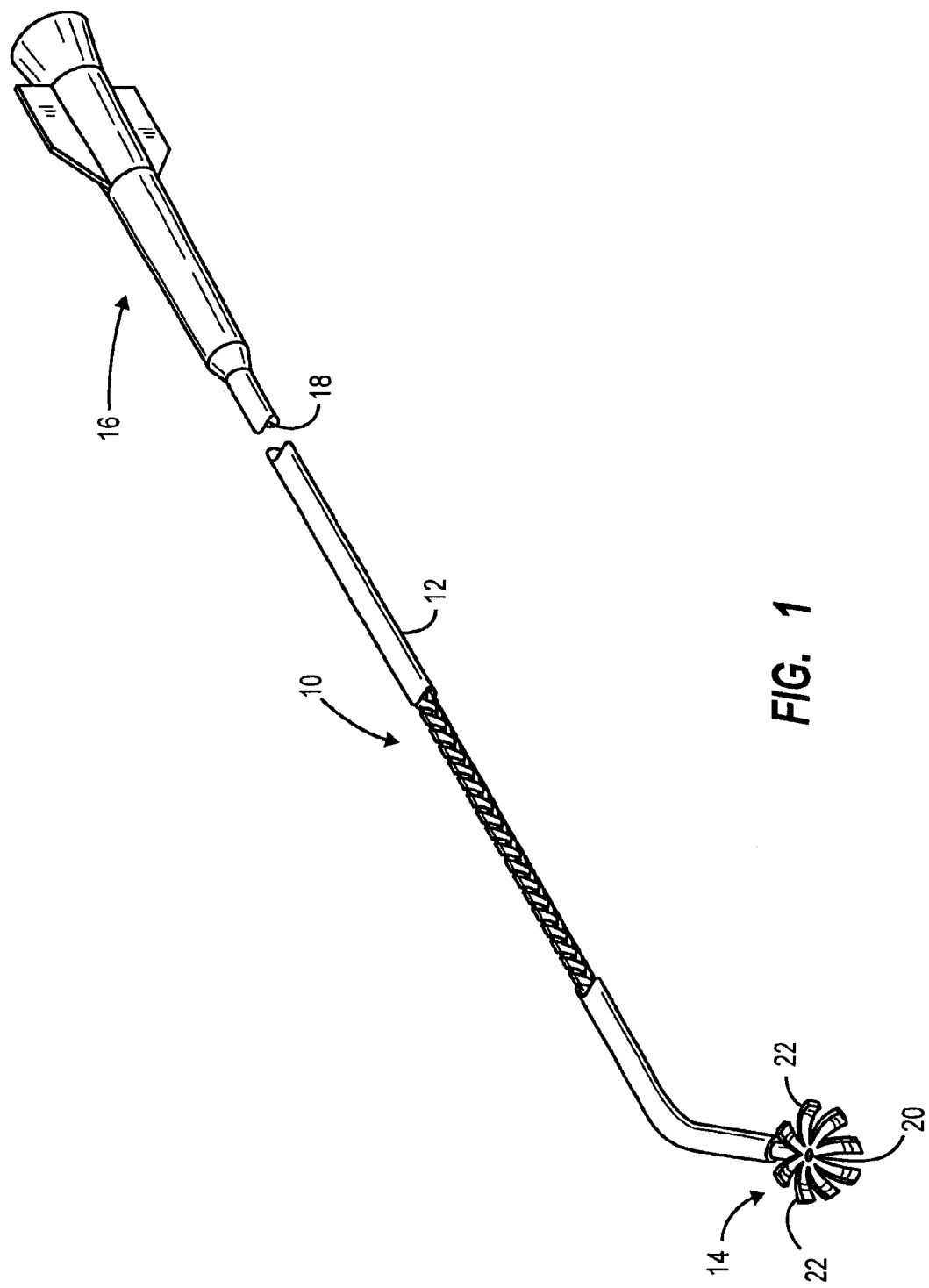
FIG. 1 is a perspective view of a first preferred embodiment of the distal section of the guide catheter of the present invention.
Figure 2:
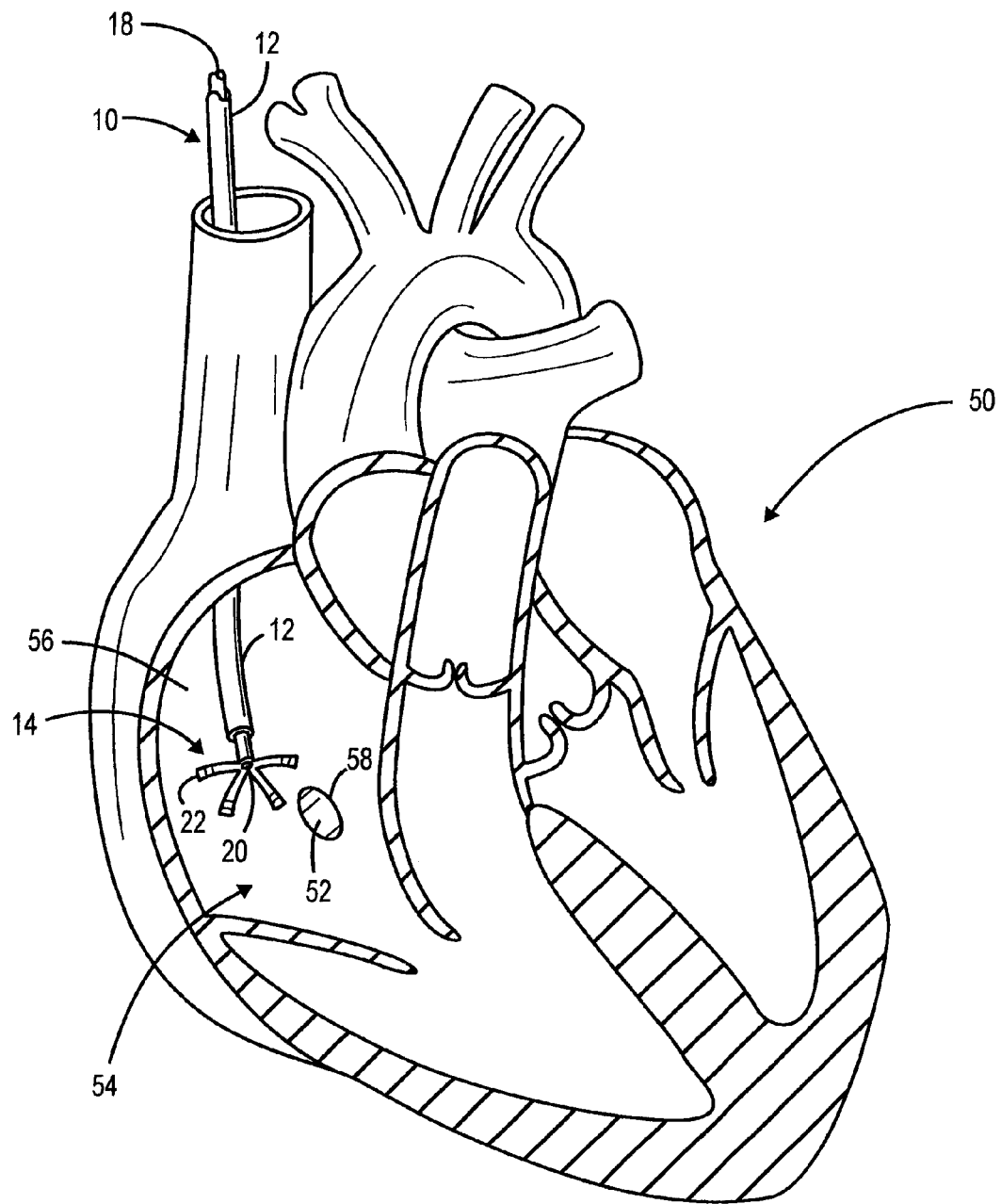
FIG. 2 is a cross-sectional view of a heart showing the distal section of the guide catheter of the present invention in contact with the atrial wall of the heart.
Figure 3:
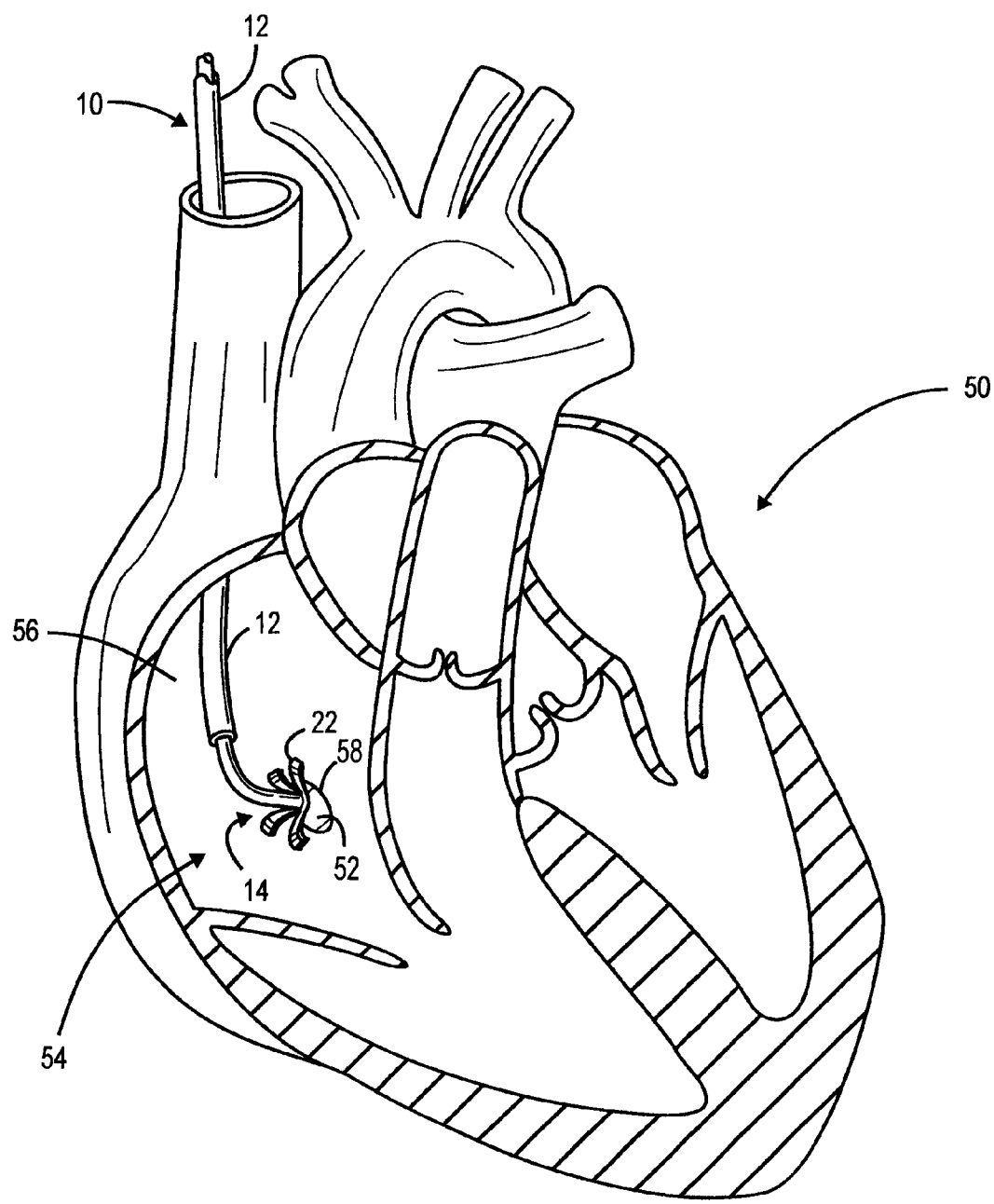
FIG. 3 is a cross-sectional view of a heart showing the tip of the guide catheter seated in the coronary sinus of the heart.

As shown in FIGS. 1–3, the apparatus of a first preferred embodiment of the present invention is an improved guide catheter 10. The guide catheter 10 has an elongated tube 12 having a distal end 14 and a proximal end 16. The tube 12 has a central lumen 18. The distal end 14 has an orifice 20 which is in communication with the central lumen 18.

The guide catheter 10 of the present invention is constructed to have the necessary size, shape and flexibility to permit the distal end 14 of the elongated tube 10 to be inserted into the heart 50 and, more specifically, into the coronary sinus 52 of the heart. Either a superior or inferior vena cava approach can be used to advance the distal end 14 into the atrium 54 of the heart. From there, the surgeon can probe the atrial wall 56 until the ostium 58 of the coronary sinus 52 is located.

To assist in locating the ostium 58, the guide catheter 10 of the present invention has a plurality of fingers 22 that extend from the distal end 14 of the elongated tube 12. As shown in FIG. 1, fingers 22 surround the orifice 20 of the distal end 14 and project distally from the distal end 14 of the elongated tube 12. The fingers 22 should be made of a soft, flexible material. One simple way to form the fingers 22 is cut slits in the distal end 14 of the elongated tube 12.

As shown in FIG. 2, the fingers 22 spread out when they contact the atrial wall 56. This serves to increase the area of the distal end of the guide catheter 10 so that it is larger than the distal end 14 of the elongated tube 12. By providing an increased surface area in contact with the atrial wall 56, the surgeon can more easily locate the ostium 58. The surgeon simply sweeps the fingers 22 across the wall 56 until the ostium 58 is located.

Once the ostium 58 is located, the surgeon advances the guide catheter 10 through the ostium 58 and into the coronary sinus 52. The fingers are sufficiently flexible that they fold back against the elongated tube 12 so they reside between the elongated tube 12 and the wall of the coronary sinus 52 as shown in FIG. 3. When so positioned, the lumen 18 and orifice 20 serve as a direct path for placement of a guidewire or cardiac lead into the coronary sinus 52.

Figure 5:
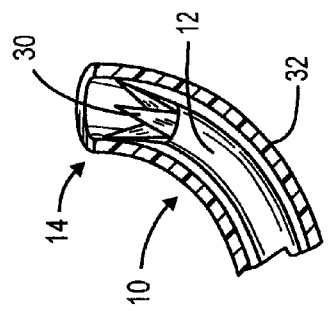
FIG. 5 is a side view of the guide catheter shown in FIG. 4 with the sheath of the guide catheter extended to cover the tines at the distal end of the guide catheter.
Figure 4:
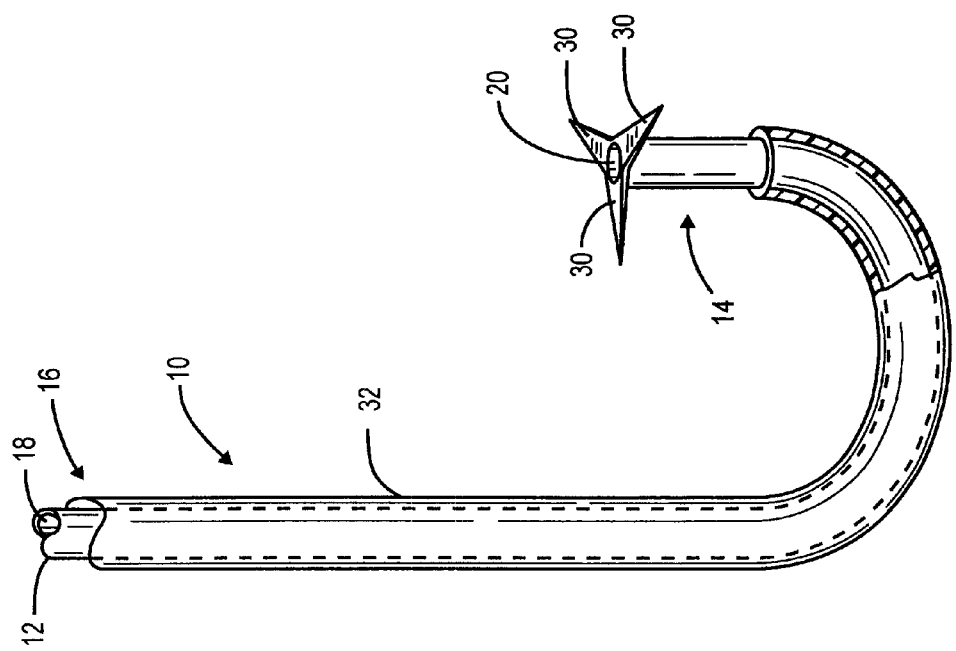
FIG. 4 is a perspective view of a second preferred embodiment of the distal section of a guide catheter made in conformance with the present invention.
Figure 6:
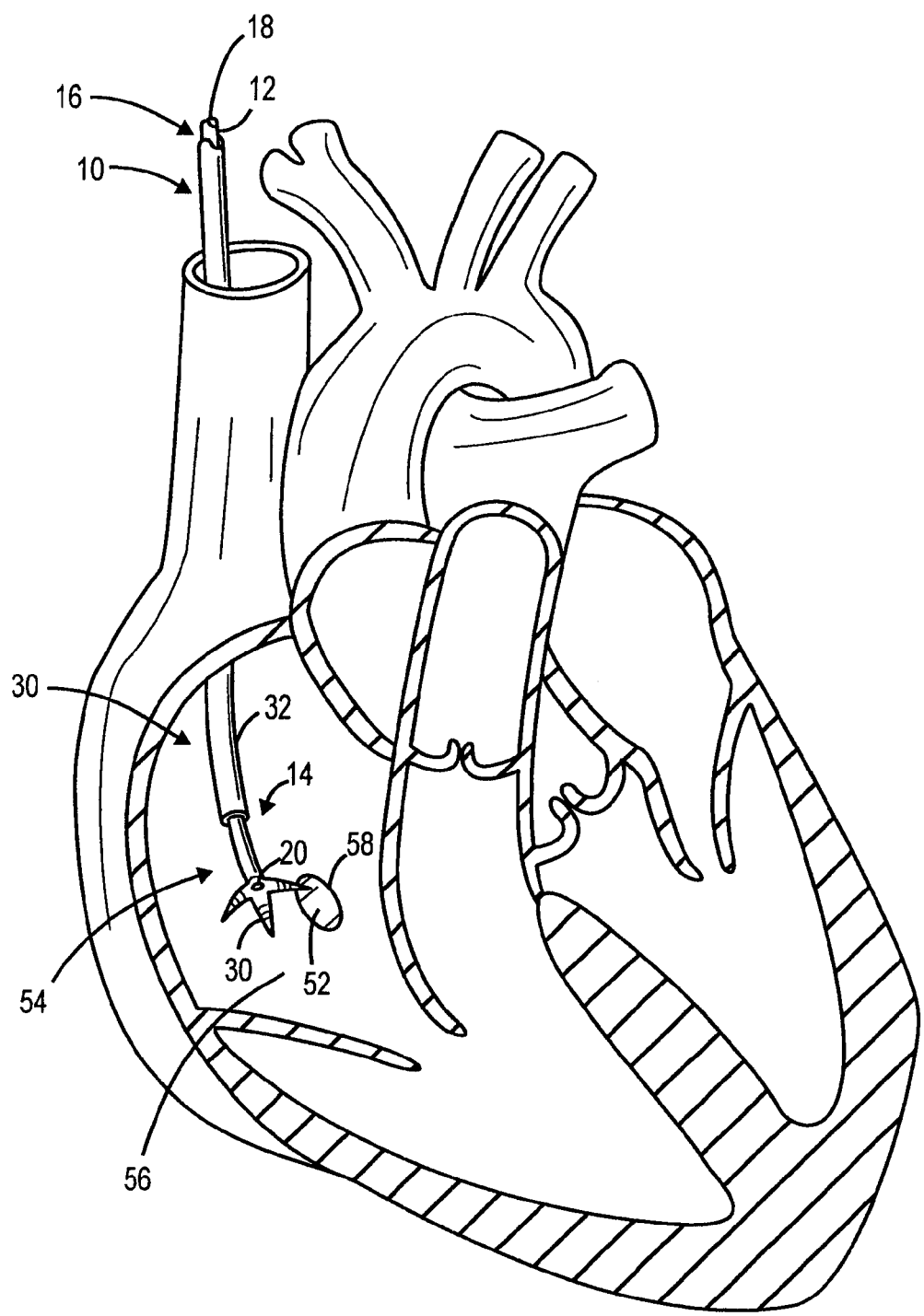
FIG. 6 is a cross-sectional view of a portion of the heart showing the tines of the guide catheter of FIG. 4 being used to anchor the guide catheter to the ostium.

A second embodiment of the present invention is shown in FIGS. 4–6. In this embodiment, a guide catheter 10 is provided. The guide catheter 10 includes an elongated body 12. The body 12 has a distal end 14, a proximal end 16, a lumen 18 and an orifice 20 at the distal end 14. The lumen 18 is in communication with the orifice 20 that extends through the elongated body 12 from the proximal end 16 to the distal end 14. The elongated body 12 can be constructed from a variety of materials including, but not limited to, polytetrafluoroethylene or polyurethane. The material selected must be non-toxic and provide an elongated body that is sufficiently flexible to follow the vasculature of the heart in an atraumatic fashion.

As is also shown in FIG. 4, the guide catheter includes a plurality of tines 30 which project outwardly from the distal end 14 of the elongated body 12. The tines 30 are flexible and projected outwardly from the elongated body 12. The tines 30 can be made of a variety of materials including, but not limited to, silicone, nylon or polyurethane materials.

As also shown in FIG. 4, the guide catheter 10 includes a sheath 32. The sheath 32 is a highly flexible tube that surrounds (i.e. is coaxial with) the elongated body 12. The sheath 32 is designed so that it can be moved back and forth between the retracted position in FIG. 4 where the tines 30 are exposed and the extended position shown in FIG. 5 where the tines 30 are covered. The sheath 32 serves to bend the tines 30 back toward each other and distally of the distal end 14 of the elongated body 12. The exterior of the elongated body and the interior of the sheath are preferably designed so that the sheath 32 can easily slide between the retracted and extended position over the elongated body 12.

Use of the guide catheter 10 shown in FIG. 4 to implant a cardiac lead into the coronary sinus of the heart will now be described with reference to FIG. 6. Shown in FIG. 6 are the right atrium 54 of the heart, the atrial wall 56, the coronary sinus 52 that leads to the left side of the heart, and the ostium 58 in the atrial wall 56 that serves as a passageway between the right atrium 54 and the coronary sinus 52. With the sheath 32 in the extended position so that the tines 30 are covered, the guide catheter is advanced so that its distal end 14 resides in the right atrium 54. The sheath 32 is then retracted to expose the tines 30. The sheath 32 can also be retracted and extended over a distal bend in the elongated body 12 to help steer the guide catheter 10 through the blood vessels. With the tines 30 exposed, the physician sweeps the distal end 14 across the atrial wall 56 until one of the tines 30 catches on the ostium 58. With at least one of the tines 30 serving to anchor the guide catheter to the ostium 58, the distal end of a guidewire (not shown) is then advanced from the proximal end of the elongated tube 12 through the lumen 18 and out the orifice 20 into the coronary sinus 52. The sheath 32 is then extended over the tines 30 and the distal end of the guide catheter is advanced over the guidewire into and through the coronary sinus until the desired position in the vasculature of the heart is reached. The guidewire is then retracted from the lumen 18 of the guide catheter. A cardiac lead (not shown) can then be passed through the lumen 18 and orifice 20 into the correct position for delivery of therapeutic pulses to the heart from a pacemaker or defibrillator (also not shown).

FIG. 7 shows a third embodiment of the present invention. This embodiment includes a guide catheter 10 having an elongated body 12 with a proximal end 16, a distal end 14, and a lumen 18 extending from the proximal end 16 to an orifice 20 in the distal end 14. Projecting from the distal end 14 is a spring 40 that is easily deflected. The spring 40 can be made of any suitable material, such as spring steel or nitinol. The spring can be covered from the inside and outside by a soft material. Alternatively, the spring 40 can be made of the same polymer material as the elongated body 12. In either case, the spring provides a pliable tip which has an accordion or bellows configuration. The length of the spring 40 can vary, but preferably will be in the range of 1 cm to 5 cm in length. When extended, the spring 40 should have an outer diameter that is approximately the same as the outer diameter of the elongated body 12. There is a central passageway through the center of the spring 40 that has a diameter approximately the same as the orifice 20 of the elongated body 12.

When the guide catheter 10 of this embodiment is used, the spring 40 assists the physician in locating the ostium 58 in the atrial wall 56 that leads to the coronary sinus 52. Specifically, when the spring 40 contacts the atrial wall 56 it is compressed or deflected. When the spring reaches the coronary sinus 52 it releases and extends into the ostium 58. The spring 40 can be used to engage the ostium 58 so that a guidewire (not shown) can be advanced through the lumen 18 and orifice 20 of the elongated body 12 and the passageway of the spring 40 into the coronary sinus. The guide catheter 10 can then be advanced into the coronary sinus 52 by sliding it over the guidewire. Once the guide catheter 10 is positioned properly, the guidewire is retracted and a cardiac lead is advanced through the lumen 18, orifice 20 and passageway of the spring 40 into position. The guide catheter 10 is then retracted. A sheath 32 can also be provided to cover the spring 40 and help steer the catheter through the vasculature of the heart. In FIG. 7, the sheath is shown in the retracted position.

FIG. 8 shows an embodiment that includes the advantages of both the second and third embodiments discussed above. Specifically, FIG. 8 shows the distal end 14 of a guide catheter 10 having an elongated tubular body 12. The distal end 14 has an orifice 20. The tubular body 12 has a lumen 18 that is in communication with the orifice 20 and extends from the proximal end to the distal end 14. Projecting from the distal end 14 of the tubular body 12 is a soft spring 70. The spring 70 can be made of steel or some other suitable material and covered inside and out with a soft, flexible material. Alternatively, it can be formed of the same material as the tubular body 12. The spring 70 has generally the same outside diameter as the tubular body 12. The spring also has a passageway 72 that extends from the tubular body 12 to the distal end 74 of the spring 70. The passageway 72 has generally the same diameter as the orifice 20 in the elongated body 12.

As shown in FIG. 8, the spring 70 has a plurality of tines 76 that project outwardly from the distal end 74 of the spring 70. These tines 76 can again be used to engage the ostium and anchor the guide catheter 10 to the ostium. A sheath can also be provided to cover the tines 76 when it is desirable to do so.

The foregoing discussion is intended to illustrate the preferred embodiment of the invention. Various modifications can be made without departing from the invention. For example, radiopaque markers can be added to the elongated body, or fingers to help the physician visualize the position of the lead. Thus, the invention is limited only by the scope of the following claims which are intended to cover all alternative embodiments and modifications that fall within the true scope of the invention.

What is claimed:

1. A guide catheter used to insert a cardiac lead through the ostium in the atrial wall of the heart that leads to a coronary sinus, said guide catheter comprising:
   a. an elongated tube having a proximal end, a distal end, an orifice in said distal end, and a lumen extending from said orifice to said proximal end such that a cardiac lead may be advanced through the lumen and orifice past the guide catheter, said elongated tube having a size, shape and flexibility which permits the distal end of said elongated tube to be advanced into the coronary sinus of the heart;
   b. a flexible member associated with the distal end of said elongated tube which assists in locating the ostium and anchoring the distal end of the guide catheter to the ostium, said flexible member comprising a spring; and
   c. a plurality of tines projecting from said spring.

2. The guide catheter of claim 1 wherein said spring is made of the same material as the elongated tube.

3. The guide catheter of claim 1 wherein said spring is covered by a soft material.

4. The guide catheter of claim 1 further including a sheath movable between an extended position covering said tines and a retracted position wherein said tines are not covered by said sheath.

5. A guide catheter used to insert a cardiac lead through the ostium in the atrial wall of the heart that leads to the coronary sinus, said guide catheter comprising:
   a. an elongated tube having a proximal end, a distal end, an orifice in said distal end, and a lumen extending from said orifice to said proximal end such that the cardiac lead may be advanced through the lumen and orifice past the guide catheter, said elongated tube having a size, shape and flexibility which permits the distal end of said elongated tube to be advanced into the coronary sinus of the heart;
   b. a flexible spring associated with the distal end of said elongated tube which assists in locating the ostium, said spring having an outer diameter substantially the same as the outer diameter of the elongated tube and a passageway through the interior of the spring and in communication with the orifice having a diameter substantially the same as the diameter of the orifice; and
   c. a plurality of tines projecting from said spring.

6. The guide catheter of claim 5 further including a sheath movable between a first extended position wherein said sheath covers said tines and a second retracted position wherein said sheath does not cover said tines.

7. A guide catheter used to insert a cardiac lead through the ostium in the atrial wall of the heart that leads to the coronary sinus, said guide catheter comprising:
   a. an elongated tube having a proximal end, a distal end, an orifice in said distal end, and a lumen extending from said orifice to said proximal end such that the cardiac lead may be advanced through the lumen and orifice past the guide catheter, said elongated tube having a size, shape and flexibility which permits the distal end of said elongated tube to be advanced into the coronary sinus of the heart; and b. a flexible spring associated with the distal end of said elongated tube, said spring having a passageway extending along its length in communication with the orifice of the elongated tube; and c. a plurality of tines projecting outwardly from said spring, said spring and said tines cooperating to assist in locating the ostium and anchoring the distal end of the guide catheter to the ostium.

8. A method for locating the ostium of the atrial wall of a heart that leads to the coronary sinus and inserting the distal end of a guide catheter through the ostium into the coronary sinus, said method comprising:

a. providing a guide catheter having an elongated tube, said elongated tube having (i) a proximal end, a distal end, an orifice in said distal end and a lumen extending from said orifice to said proximal end; and (ii) a flexible member associated with the distal end of said elongated tube which assists in locating the ostium and anchoring the distal end of the guide catheter to the ostium;

b. inserting the distal end of the elongated tube into the right atrium of the heart;

c. moving the flexible member associated with the distal end of said elongated tube across the atrial wall to locate the ostium;

d. using said flexible member to anchor the distal end of the elongated tube to the ostium;

e. passing a guidewire through the orifice in the distal end of the elongated tube and into the coronary sinus; and f. advancing the guide catheter over the guidewire into the coronary sinus.

9. A method for locating the ostium in the atrial wall of a heart that leads to the coronary sinus and inserting the distal end of a guide catheter through the ostium and into the coronary sinus comprising:

a. providing a guide catheter having (i) an elongated tube, said elongated tube having a proximal end and a distal end, an orifice in said distal end and a lumen extending from said orifice to said proximal end; and (ii) a plurality of flexible fingers extending distally from the distal end of the elongated tube;

b. inserting the distal end of the elongated tube into the right atrium of the heart;

c. sweeping said fingers across the atrial wall to locate the ostium; and d. inserting the distal end of the elongated tube through the ostium in the atrial wall and into the coronary sinus.

* * * * *